United States Patent [19]

Bergeron

[11] Patent Number: 4,750,478
[45] Date of Patent: Jun. 14, 1988

[54] SEAT SUPPORT AND RESTRAINT SYSTEM FOR THE HANDICAPPED

[76] Inventor: Timothy J. Bergeron, R.D. 1, Box 40, Dolgeville, N.Y. 13329

[21] Appl. No.: 874,032

[22] Filed: Jun. 13, 1986

[51] Int. Cl.[4] ............................ A61F 5/01; A61F 5/00
[52] U.S. Cl. ......................................... 128/70; 128/78
[58] Field of Search .................. 297/DIG. 1, DIG. 2, 297/188, 192, 250, 258, 259, 260, 429, 430, 464, 135; 128/68, 69, 70, 78

[56] References Cited

U.S. PATENT DOCUMENTS

| | | | |
|---|---|---|---|
| 513,169 | 1/1894 | Armstrong | 297/430 |
| 961,715 | 6/1910 | Christianson | 297/430 |
| 1,739,366 | 12/1929 | Lang | 297/250 |
| 2,375,696 | 5/1945 | Shick | 297/429 |
| 2,503,942 | 4/1950 | Engelberg et al. | 155/44 |
| 2,535,212 | 12/1950 | Johnson | 155/127 |
| 2,546,765 | 3/1951 | McKinley | 155/28 |
| 2,630,160 | 3/1953 | Friedman | 155/30 |
| 2,786,512 | 3/1957 | Moyer | 297/430 |
| 2,860,691 | 11/1958 | Caeser | 297/DIG. 1 |
| 2,947,350 | 8/1960 | Davis | 155/152 |
| 3,269,768 | 8/1966 | Kinney | 297/68 |
| 3,376,070 | 4/1968 | Johnson | 297/459 |
| 3,497,259 | 2/1970 | Sherfey | 297/391 |
| 3,672,722 | 6/1972 | Murcott | 297/437 |
| 3,762,768 | 10/1973 | Hyde et al. | 297/253 |
| 3,910,634 | 10/1975 | Morris | 297/250 |
| 3,937,490 | 2/1976 | Nasr | 280/242 |
| 3,941,418 | 3/1976 | Bernard | 297/DIG. 2 |
| 3,948,556 | 4/1976 | Hyde et al. | 297/250 |
| 4,300,249 | 11/1981 | Taylor | 4/661 |
| 4,339,013 | 7/1982 | Weigt | 180/6.5 |
| 4,367,897 | 1/1983 | Cousins | 297/284 |
| 4,383,713 | 5/1983 | Roston | 297/464 |
| 4,429,916 | 2/1984 | Hyde et al. | 297/250 |
| 4,451,082 | 5/1984 | Giordani | 297/90 |
| 4,545,613 | 10/1985 | Martel et al. | 297/250 |

FOREIGN PATENT DOCUMENTS

| | | | |
|---|---|---|---|
| 2048326 | 4/1972 | Fed. Rep. of Germany | 297/DIG. 2 |
| 1519793 | 8/1978 | United Kingdom | 297/250 |

OTHER PUBLICATIONS

MPI Literature, Medical Equipment Distributors, Inc., "Seating System for Children with Cerebral Palsy".

Primary Examiner—Edgar S. Burr
Assistant Examiner—Tonya Lamb
Attorney, Agent, or Firm—Heslin & Rothenberg

[57] ABSTRACT

A portable seat support and restraint system intended to be positioned on a conventional seating surface is comprised of a contoured chair having molded base and back portions. The base and back portions form a substantially continuous support surface capable of positioning an occupant's pelvis in a fixed position and properly aligning an occupant's muscles and skeletal frame. In addition, the seat support and restraint system includes an adjustable frame internal to the base and back portions of the contoured chair, independent footrest and tray assemblies adjustably secured to the base portion and a headrest adjustably secured to the back portion of the contoured chair.

40 Claims, 5 Drawing Sheets

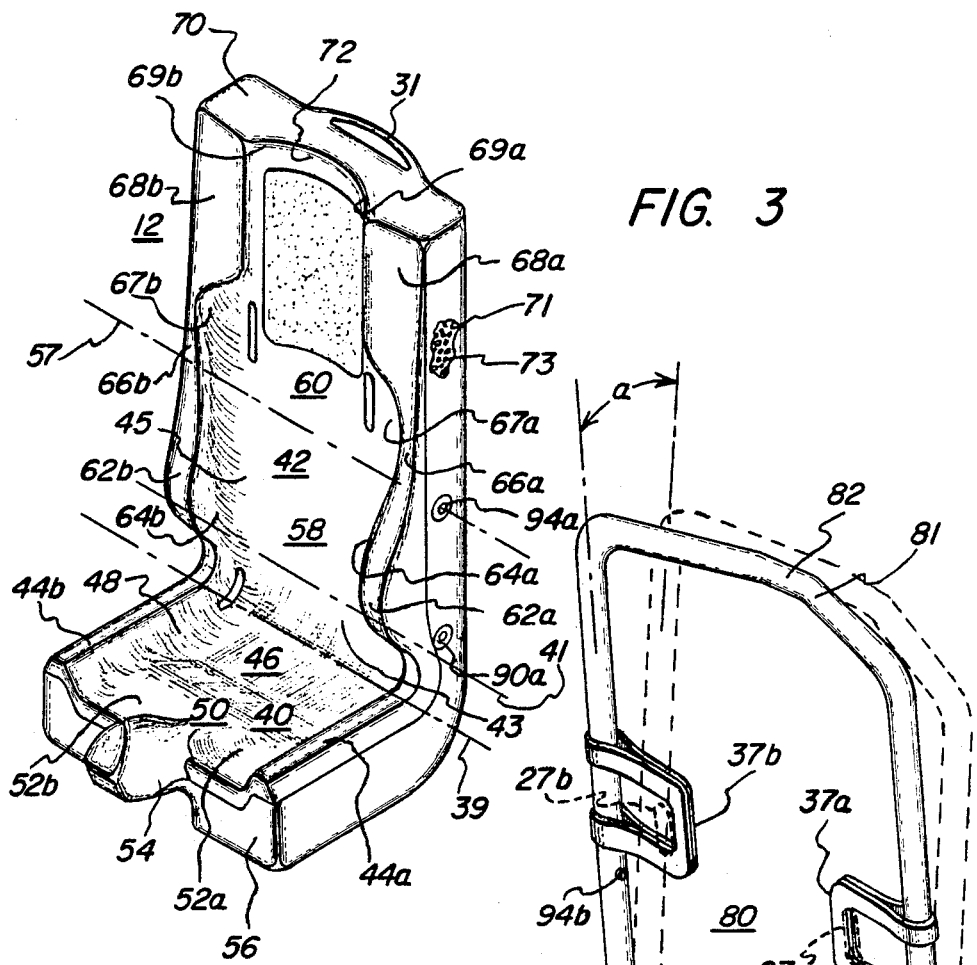
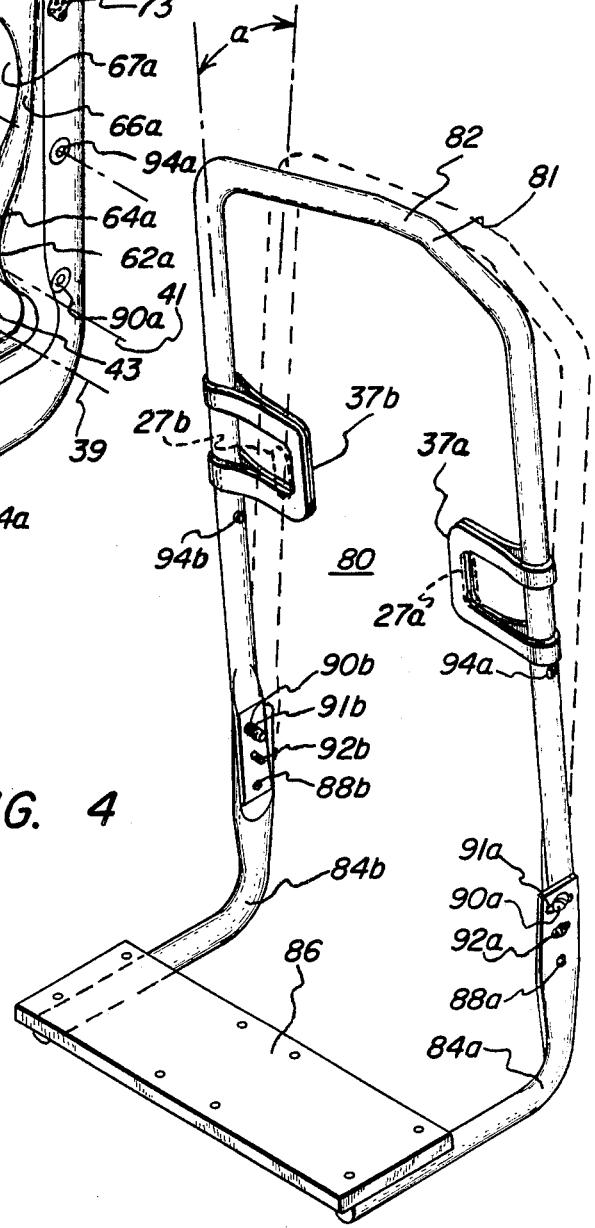

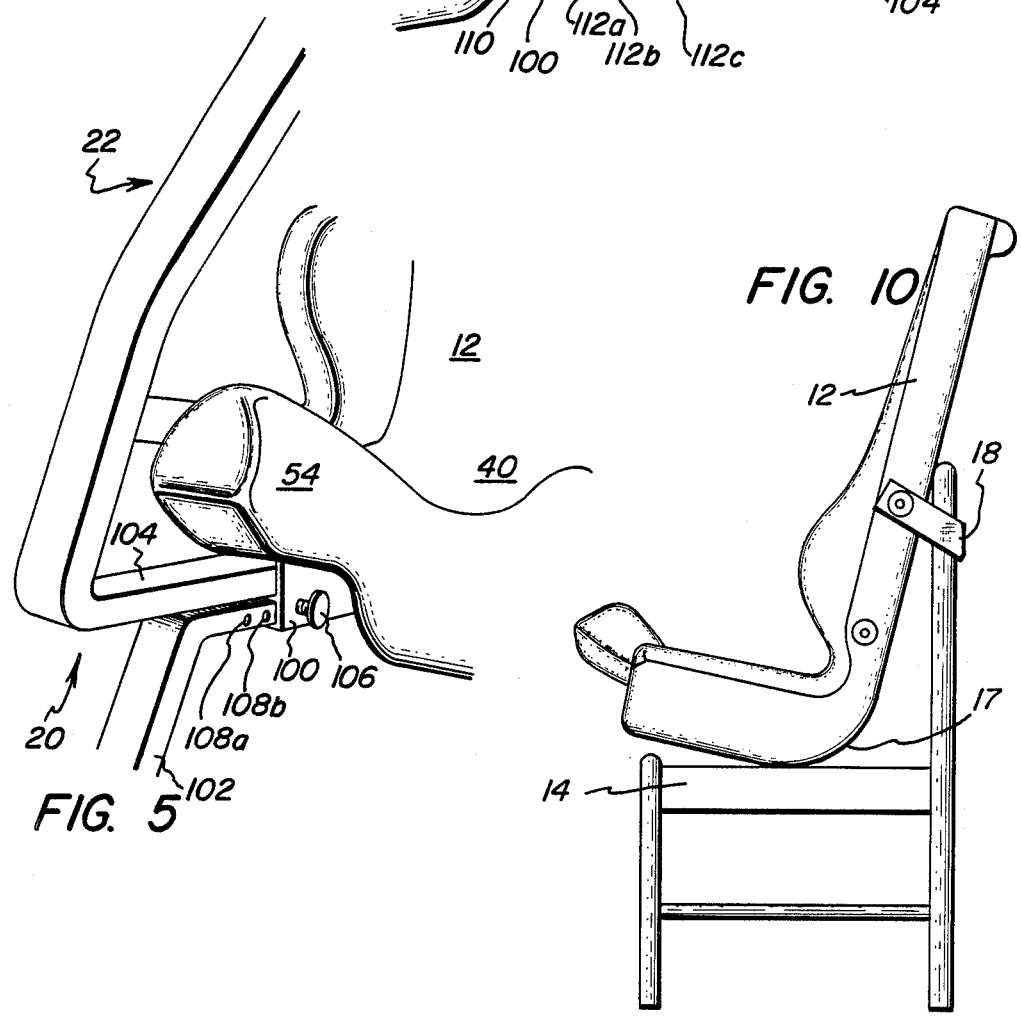
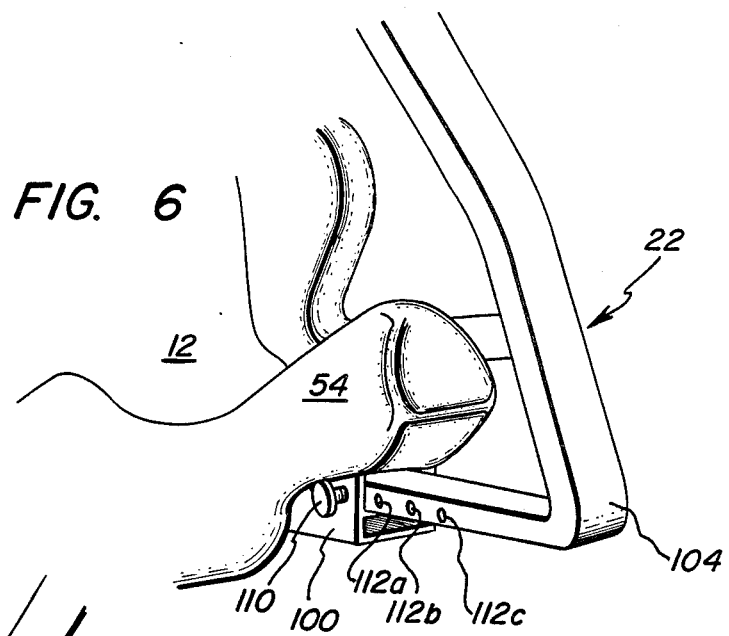

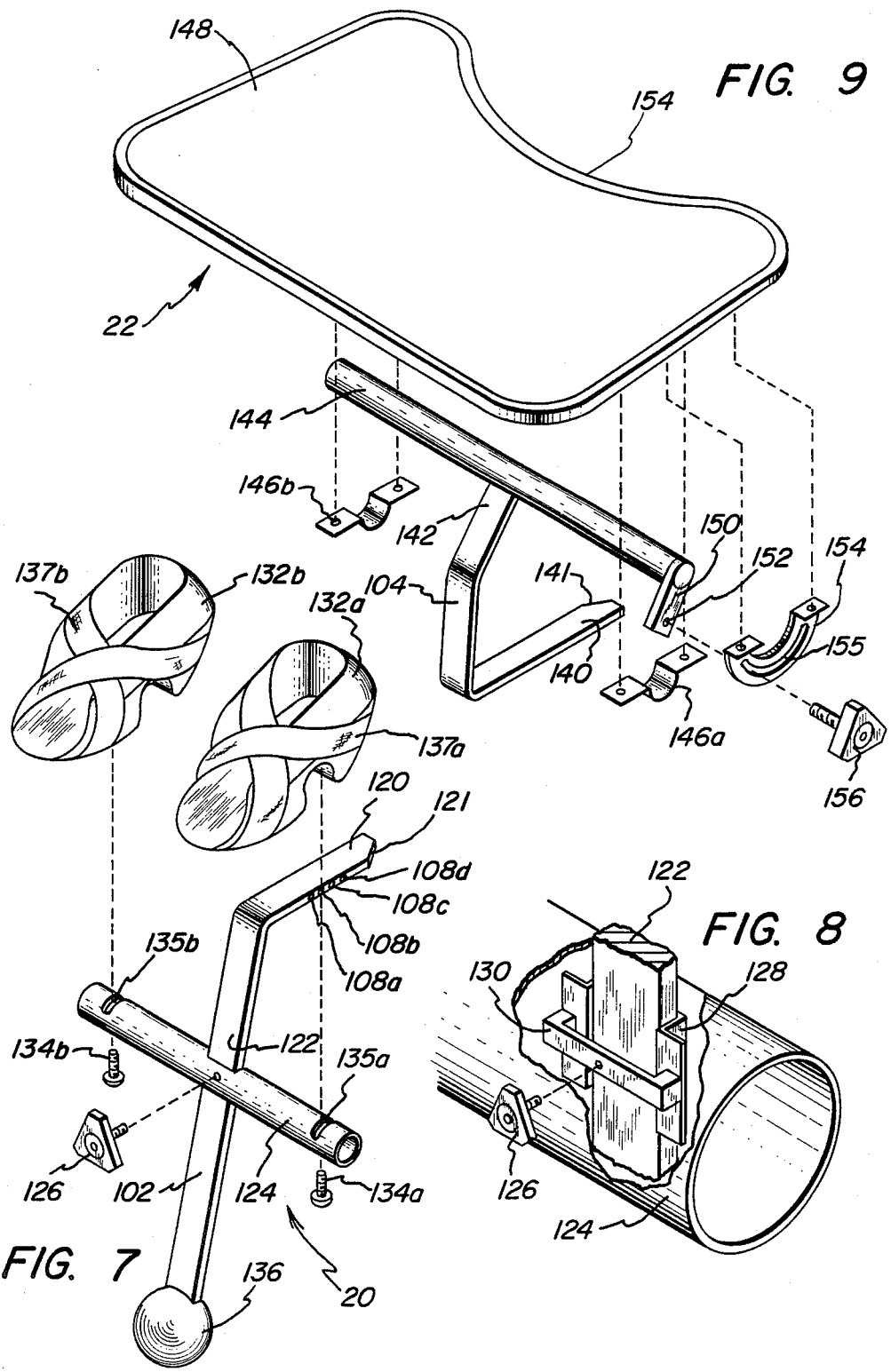

SEAT SUPPORT AND RESTRAINT SYSTEM FOR THE HANDICAPPED

BACKGROUND OF THE INVENTION

This invention relates generally to supportive seating for those who are handicapped and more particularly, to a seat support and restraint system capable of slowing muscle and skeletal deformation and facilitating therapy of a neurologically impaired occupant and particularly of a disabled child.

Neurologically impaired individuals suffer from injury, disease or disorder of the brain or nervous system. Two leading causes of neurological impairment, particularly in children, are cerebral palsy and muscular dystrophy. While the severity of such disorders will vary, in many cases the children suffer from characteristic symptoms such as partial or total loss of muscular control and motion, and partial loss of speech, hearing and reasoning abilities. As a result, such children often possess limited daily living skills. Additionally, such children often experience progressive muscular and skeletal deformity due to the insufficiently controlled manner in which their muscles and bones develop. Most, if not all presently available seating structures for disabled children fail to assist such a child in performing daily living skills and fail to assist in slowing the child's muscular and skeletal deformities.

There have basically been two approaches to the seating of neurologically impaired children. A first approach has been to produce customized seating for each child. A customized seat is typically produced by molding a seating surface about a child's body structure or by hand fabricating a seating surface about a child's body structure from plywood, blocked foam and vinyl. There are several drawbacks, however, to such a customized seating approach aside from the obvious cost considerations. For example, since a child's body is continually developing, a customized seat is likely to be outgrown in a relatively short interval. More importantly, however, because such seats are formed or constructed about a child's body structure, (including existing deformities) they do not assist in controlling or slowing the progress of muscular or skeletal deformities nor do they facilitate muscle therapy of a seated occupant.

A second seating approach has been to produce seating structures widely adaptable to different children. Such adaptable structures typically have several adjustable components which adapt to different children. Again, however, there are several drawbacks to such an approach. Since these seats are generally adaptable, they typically consist of self contained, bulky structures which necessarily are limited in where they can be used. In addition, they are usually complicated structures to properly adjust and are difficult to maintain in proper adjustment with extended use. Also, since these seats normally have flat, adjustable support surfaces to accommodate different children, they clearly lack the contoured body support needed to control and slow muscle and skeletal deformation and facilitate therapy.

Therefore, there presently exists a genuine need for a seat support and restraint system capable of properly aligning a neurologically impaired child's body so as to improve the child's daily living skills, slow the child's progressive muscular and skeletal deterioration and facilitate therapy.

SUMMARY OF THE INVENTION

Accordingly, a principal object of the present invention is to provide a seat support and restraint system capable of controlling and slowing deterioration of an occupant's muscles and bones from a normal to abnormal condition.

Another object of the present invention is to provide such a seat support and restraint system which is adjustable to accommodate different occupants.

Still another object of the present invention is to provide a seat support and restraint system which is transportable for use in various environments.

Yet another object of the present invention is to provide such a seat support and restraint system which is capable of enhancing an occupant's social esteem.

It is a further object of the present invention to provide a seat support and restraint system capable of properly positioning an occupant with a minimum of adjustments.

It is a still further object of the present invention to provide a seat support and restraint system capable of improving an occupant's performance of daily living skills.

The present invention accomplishes these objects by providing a portable and adjustable seat support and restraint system designed to be positioned on a conventional seating surface when in use. In one aspect, the seat support and restraint system includes a contoured chair having molded base and back portions which form a continuous support surface. The base portion has a first pair of side walls and a seating surface including a rearward section and a forward section. The rearward section is recessed below the forward section and is connected thereto by a continuous inclined ridge. The forward section has a pair of troughs running forwardly from the rearward section which are separated by a central ridge. The back portion of the contoured chair has a support surface including a lower section and an upper section. The lower section has a second pair of side walls which have inwardly sloping surfaces therefrom. The upper section has a third pair of side walls continuous with and protruding less than, the second pair of side walls, and each side wall of said third pair terminates in an enlarged portion in opposed relation to the other so as to define a central cradle. The upper section further includes gradually inwardly sloping surfaces from said third pair of side walls. The molded base and back portions of the contoured chair are designed to cooperate in such a manner so as to firmly plant an occupant's pelvis and to properly align an occupant's muscles and bones.

In another aspect, the seat support and restraint system of the present invention includes a contoured, portable chair having base and back portions molded of a resilient foam material such that the base and back portions form a substantially continuous support surface. Internal to the contoured, portable chair is a frame structure having a substantially straight top portion and an L-shaped bottom portion which are pivotally adjustable relative to each other. In addition, an adjustable footrest assembly is secured to the base portion of the contoured chair and a headrest is adjustably secured to the back portion of the contoured chair. In this aspect of the seat support and restraint system, the contoured chair and internal frame, footrest assembly and headrest adjustments cooperate to firmly plant an occupant's pelvis and properly align an occupant's muscles of daily living skills, thereby facilitating the performance of daily living skills, slowing muscle and skeletal deterioration and facilitating therapy of the seated occupant.

BRIEF DESCRIPTION OF THE DRAWING

While the specification concludes with claims particularly pointing out and distinctly claiming the present invention, the objects, features and advantages of the present invention can be more readily ascertained from the following detailed description of one preferred embodiment when read in conjunction with the accompanying drawings in which:

FIG. 3 is a perspective view of the contoured chair of the seat support and restraint system shown in FIG. 1;

FIG. 4 is a perspective view of one embodiment of a frame internal to the contoured chair shown in FIG. 3;

FIG. 5 is a partially enlarged perspective view of the front end of the contoured chair shown in FIG. 3 with the tray assembly and footrest assembly secured thereto;

FIG. 6 is a partially enlarged perspective view from the opposite side of the contouured chair shown in FIG. 5 with only the tray assembly secured thereto;

FIG. 7 is an exploded perspective view of the footrest assembly of the seat support and restraint system shown in FIG. 1;

FIG. 8 is an enlarged, cut-away perspective view of a brake mechanism useful in implementing the footrest assembly shown in FIG. 7;

FIG. 9 is an exploded perspective view of the tray assembly of the seat support and restraint system shown in FIG. 1; and FIG. 10 is a side elevational view of the seat support and restraint system of FIG. 1 shown secured to a conventional seating structure in an alternative position from that shown in FIG. 1.

DETAILED DESCRIPTION OF THE INVENTION

Figure 1:
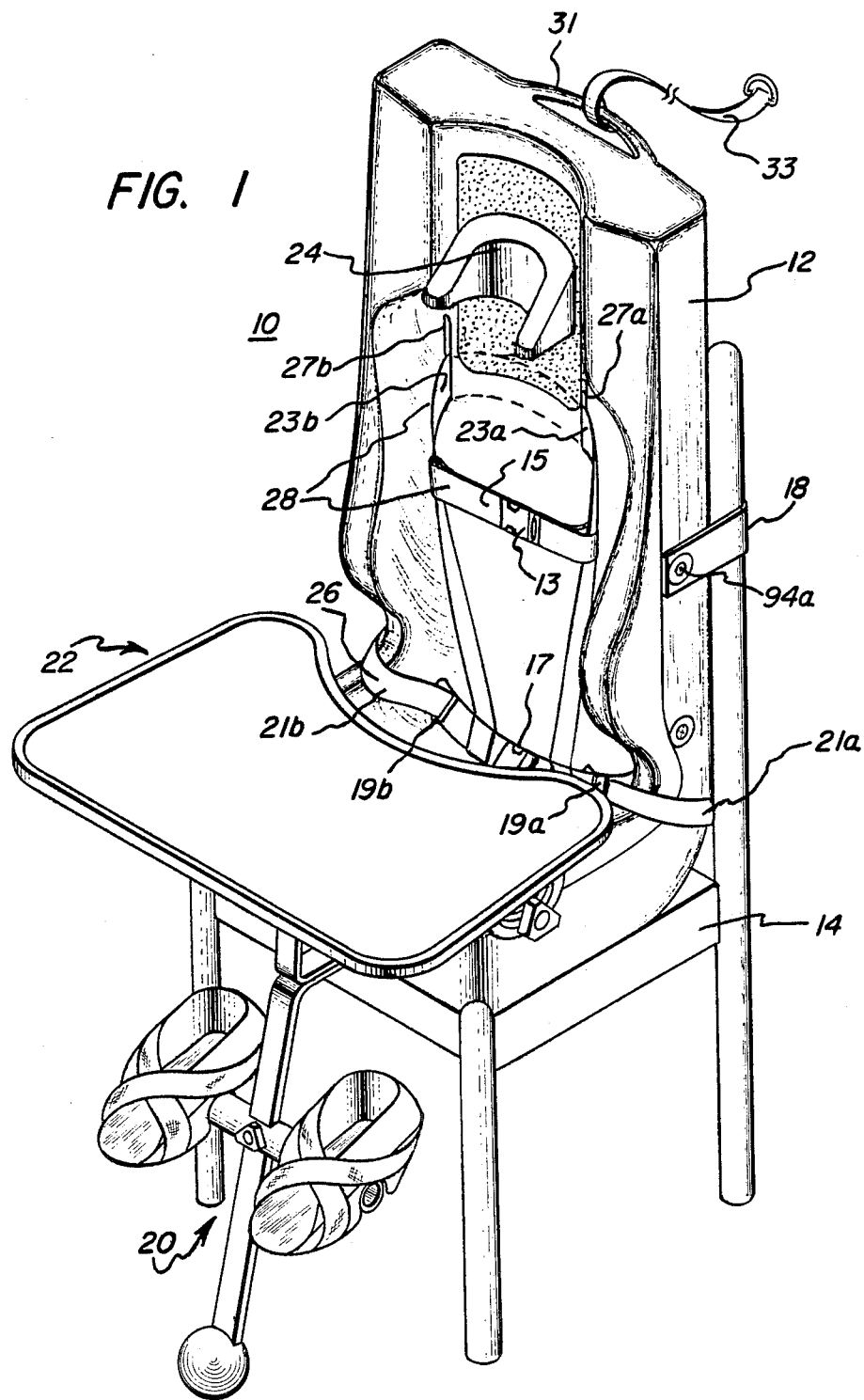
FIG. 1 is a perspective view of one embodiment of a seat support and restraint system of the present invention shown secured to a conventional seating structure.

One preferred embodiment of the seat support and restraint system of the present invention, generally denoted as 10, is shown perspectively in FIG. 1. Seat support and restraint system 10 includes a portable, contoured chair 12 shown resting on a conventional seating structure 14 and secured thereto by adjustable belt strap 18. Belt strap 18 is secured to contoured chair 12 on one side by securing screw 94a and on the opposite side by securing screw 94b (not shown) both of which are removable in order to provide attachment points for additional strapping or customized add ons. Contoured chair 12 is securable to various types of conventional seating structures (such as wheelchairs, strollers, school room chairs, etc.) and securable to any particular seating structure in a plurality of positions as discussed below. As more clearly shown in FIG. 2, removably attached to contoured chair 12 are: footrest assembly 20, tray assembly 22, headrest 24, lap belt 26, shoulder/trunk belt 28 and tether strap 33. Footrest assembly 20 and tray assembly 22 are discussed in detail below with reference to FIGS. 5–9.

Headrest 24 preferably has a U-shaped face 30 for matable engagement with an occupant's head and/or neck. Attached to the curved backside 34 of headrest 24 is a hook-type fabric 32 which is capable of detachably engaging a loop-type fabric 36 secured to contoured chair 12 in an appropriate location. A relatively large surface area of loop-type fabric 36 provides a wide range of attachment points for headrest 24 and thus facilitates proper positioning of it for different occupants of various heights. A particularly efficient hook-type fabric 32 and loop-type fabric 36 combination is commercially available under the trademark "Velcro".

Lap belt 26 and shoulder/trunk belt 28 are adjustable to accommodate occupants of various heights and weights. Each side 21a and 21b of lap belt 26 is looped around one side of chair 12 through appropriately sized inner openings 25a (not shown) and 25b, respectively, near the base of chair 12. Lap belt sides 21a and 21b each include a slide adjustment mechanism 19a and 19b, respectively. A centrally positioned, standard male-female belt buckle 17 serves to lock the two sides together around an occupant. When so positioned, lap belt 26 is approximately at a 45° angle relative to the base of contoured chair 12.

Shoulder/trunk belt 28 is preferably designed to automatically adjust about the shoulders and trunk of occupants of different body height and weight. This is accomplished by allowing belt 28 to float within vertical slots 27a and 27b in the back portion of contoured chair 12. For example, belt 28 will automatically adjust upwards within slots 27a and 27b about the shoulders of a tall occupant. As shown, as dotted lines in FIGS. 1 and 2, one side 23a of belt 28 passes through slot 27a and connects around the backside of chair 12 with the other side 23b of belt 28, after passing through slot 27b. Connection of sides 23a and 23b can be accomplished in any standard manner provided belt 28 remains adjustable and removable. Each side 23a and 23b of belt 28 is secured at its bottom end to lap belt 26, and in particular, to sides 21a and 21b, respectively. In addition, sides 23a and 23b are interconnected intermediate their ends by a substantially horizontal cross belt 15 which, as shown, is preferably positioned such that it will traverse an occupant's chest when in use. A standard male-female belt buckle 13 is included with cross belt 15.

Figure 2:
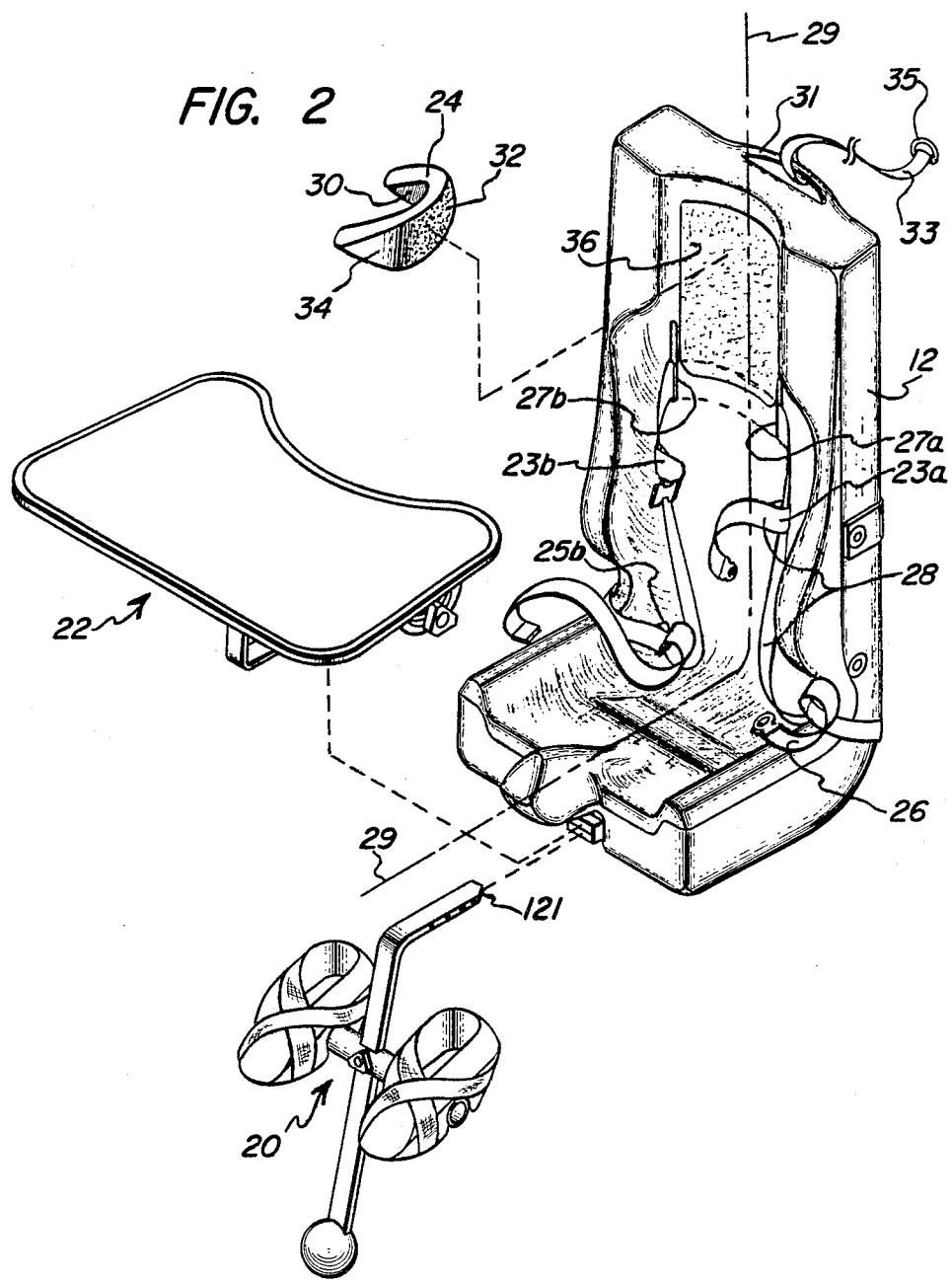
FIG. 2 is an exploded perspective view of the seat support and restraint system shown in FIG. 1.

As discussed below, lap belt 26 assists in orienting and securing an occupant's pelvis within contoured chair 12. Similarly, shoulder/trunk belt 28 assists in maintaining an occupant's trunk at midline relative to contoured chair 12. The midline of contour chair 12 is represented in FIG. 2 by imaginary line 29 running longitudinally down contoured chair 12.

Tether strap 33 is secured at one end to a handle 31 which, as discussed below, is formed integral with frame 82 near the top backside of contoured chair 12. At the other end of tether strap 33, there is affixed one portion 35 of a standard motor vehicle belt buckle. In addition, there is preferably a means for adjusting the length of tether strap 33 (not shown). Tether strap 33 is designed to assist in securing contoured chair 12 to a seating surface within a motor vehicle, consisting of either private or public transportation. For example, if contoured chair 12 is located on a front seat of an automobile, the free end of tether strap 33 may be secured to a corresponding portion of a standard motor vehicle belt buckle located in a backseat, thereby ensuring securement of the top back portion of contoured chair 12 against the front seat support surface. In addition, when so used as a car seat, the motor vehicle's front seat belt will be wrapped around contoured chair 12 near the union of its base and back portions and be located between the occupant and the seating support face of contoured chair 12. With such a chair securing arrangement lap belt 26 and shoulder/trunk belt 28 function as safety belts in addition to positioning belts.

Contoured chair 12 will now be described. Central to the design of contoured chair 12 is the principle that proper muscular and skeletal support may be obtained by building from a sound foundation, the foundation being a firmly planted and restrained pelvis. In an upperward direction from the occupant's pelvis, proper muscle and skeletal alignment is largely accomplished by the back portion of contoured chair 12 and in a downward direction by the base portion of contoured chair 12.

With reference to FIG. 3, for convenience of description contoured chair 12 is divided into base portion 40 and back portion 42 by an imaginary line 39 running laterally across contoured chair 12. Base portion 40 and back portion 42 meet in a continuous manner along imaginary line 39 in that there is no sharp division or surface relief feature between them. Base portion 40 simply flows smoothly into back portion 42.

Base portion 40 has a first pair of side walls 44a and 44b of substantially the same height and width. The height and width being sufficient to effectively position and secure an occupant's pelvis in a lateral direction and maintain an occupant's thighs in an adducted position. Each inner surface of said first pair of side walls preferably slopes inwardly and downwardly to a seating surface which includes a rearward section 46 for receiving an occupant's buttocks, an inclined ridge 48 and a forward section 50 intended to support an occupant's legs. Rearward section 46 is recessed below forward section 50 and is smoothly connected thereto by inclined ridge 48. Forward section 50 has a pair of troughs 52a and 52b partially defined and separated by a rounded central ridge 54. Central ridge 54 assists in maintaining an occupant's thighs in an abducted position. To be discussed below, central ridge 54 preferably extends beyond the front edge 56 of base portion 40.

When an occupant is properly seated on contoured chair 12, his pelvis will be firmly planted over rearward section 46 by a combined effect of back portion 42, first pair of side walls 44a and 44b, inclined ridge 48 and lap belt 26. Once an occupant's pelvis is firmly planted various muscle and skeletal groups may be properly aligned. Additionally, it should be observed that when an occupant is properly seated on contoured chair 12 with his buttocks in the rearward section, his ischial tuberosities will contact inclined ridge 48, thus preventing any forward thrusting of the occupant's pelvis.

Again, for convenience of description, back portion 42 is divided into a lower section 58 and an upper section 60 by an imaginary line 57 which runs laterally across the middle of back portion 42. As before, there is no sharp division or surface relief feature between lower section 58 and upper section 60, they simply flow smoothly into one another. Section 58 is itself divided by another imaginary line 41, which will be discussed further below. Lower section 58 has a second pair of side walls 62a and 62b continuous with the protruding more than first pair of side walls 44a and 44b in base portion 40. Each side wall of said second pair has substantially the same width and protrudes substantially the same distance out from the central support surface of back portion 42. Each inner surface 64a and 64b of second pair of side walls 62a and 62b is inwardly curved in order to maximize contact with and control over an occupant's trunk. Second pair of side walls 62a and 62b are designed and constructed to properly position and retain an occupant's trunk at midline. As mentioned earlier, shoulder/trunk belt 28 may be used to ensure maintenance of an occupant's trunk at a midline position relative to back portion 42.

Upper section 60 of back portion 42 has a third pair of side walls 66a and 66b continuous with and substantially less protruding than second pair of side walls 62a and 62b. Each side wall of said third pair 66a and 66b has substantially the same width and protrudes substantially the same distance out from the central support surface of back portion 42. Further, each side wall of said third pair 66a and 66b terminates in a substantially identical enlarged portion 68a and 68b in opposed relation to one another near the top 70 of contoured chair 12. The inner surfaces 67a and 67b of third pair of side walls 66a and 66b are gradually curved in order to matably engage an occupant's upper back and shoulder area in such a way as to slightly protract the occupant's shoulders for increased comfort and posture control over the upper body. At enlarged portions 68a and 68b each inner surface 69a and 69b of third pair of side walls 66a and 66b inwardly slope so as to form a central cradle 72 for receiving an occupant's head and neck. Loop-type fabric 36 previously mentioned in connection with FIGS. 1 and 2 is preferably secured to back portion 42 within central cradle 72. When in use, compressive forces ensure strong lateral securement of hook-type fabric 32 to loop-type fabric 36. This is principally due to the curved nature of central cradle 72 and headrest 24. As mentioned before a handle 31 is molded on the backside of contoured chair 12 near top 70. Handle 31 provides a ready means for transporting contoured chair 12 from one location to another.

Although other constructions are possible, contoured chair 12 is preferably molded of a resilient foam material 73 and provided with a durable, seamless exterior covering 71. The exterior covering is designed such that all internal joints and structures are fully encased for the occupant's protection. Since seat support and restraint system 10 of the present invention is intended to be positioned on a conventional seating surface, the thickness of contoured chair 12 is minimized by including an internal frame as a support structure. This ensures that an occupant of seat support and restraint system 10 is as close to the seating plane of the conventional seating structure as possible which in turn will tend to enhance the occupant's social esteem.

As shown in somewhat enlarged view in FIG. 4, contoured chair 12 has an L-shaped internal frame 80. Internal frame 80 has a U-shaped top portion 82 which is bent at its upper end 81 such that when seat structure 12 is molded about frame 80, said upper end extends beyond the molded foam to form handle 31 subsequent application of covering 71. Secured at each end of top portion 82 is an L-shaped bottom portion member 84a and 84b. Affixed between bottom portion members 84a and 84b is a support bar 86. This support bar structure may simply consist of a wooden block bolted at each end to bottom portion members 84a and 84b. Preferably, belt strap securing screws 94a and 94b engage internal frame 80 as shown, thus increasing the strength with which belt strap 18 is secured to contoured chair 12.

In one preferred embodiment, top portion 82 is pivotally attached at 88a and 88b near each end to bottom portion members 84a and 84b, respectively. In the embodiment shown, adjustment of top portion 82 relative to bottom portion members 84a and 84b is accomplished by loosening screws 90a and 90b secured within slots 91a and 91b, respectively, and then by retightening screws 90a and 90b after a desired angle change has been effected. Permanently positioned locking screws 92a and 92b are preferably loosely connected within their own slots below slots 91a and 91b to prevent top portion 82 from exceeding its permissible adjustment range should one or both of screws 90a and 90b be completely removed from frame 80. A 20°-30° adjustment range, a, (forward or backward) is believed sufficient for most needed therapeutic positioning and/or comfort adjustments. It should be clear that in order for internal frame 80 to be adjustable, contoured chair 12 will necessarily be manufactured of a resilient, slightly bendable material.

The importance of the particular location of pivot points 88a and 88b should be emphasized. When frame 80 is located within contoured chair 12 pivot points 88a and 88b will be positioned roughly at imaginary line 41 (see FIG. 3), which divides lower section 58 of base portion 40 into a first part 43 and a second part 45. By so locating pivot points 88a and 88b, only that portion of back portion 42 encompassing upper section 60 and an adjacent portion of lower section 58, i.e., part 45, is adjustable relative to base portion 40. This adjustment of a limited part of back portion 42 is important in that it allows an occupant's pelvis to remain substantially fixed as originally positioned within contoured chair 12 even while back adjustments are made. If, on the other hand, back adjustment pivot points are located close to imaginary line 39 the position of an occupant's pelvis would necessarily be changed as back adjustments are made since the bottom part of lower section 58 assists in the positioning of the occupant's pelvis.

Lastly with reference to FIG. 4, positioned internally to contoured chair 12 are flexible loop belts 37a and 37b encircling opposed upright members of frame 80 and vertical slots 27a and 27b, respectively, as shown. Loop belts 37a and 37b may be so positioned by placing the belts about the upright members of frame 80 and the forming mold projections (not shown) which create vertical slots 27a and 27b in contoured chair 12 prior to molding contoured chair 12. The belts 37a and 37b are included since, as noted above, chair 12 is preferably molded of resilent foam material 73, which typically comprises a low tear resistent substance. Through cooperation with shoulder/trunk belt 28 passing through internally molded loop belts 37a and 37b, i.e., because belts 37a and 37b encircle slots 27a and 27b once chair 12 is molded, increased occupant restraint is, therefore, achieved should a motor vehicle accident occur when contoured chair 12 is secured therein. Additionally, depending upon the method of affixing lap belt 26 to contoured chair 12, it may be desirable to incorporate similar loop belts within contoured chair 12, in a similar manner to loop belts 37a and 37b for securing lap belt 26 to frame 80.

As mentioned previously, removably secured to contoured chair 12 are footrest assembly 20 and tray assembly 22. One method of removably securing these assemblies to contoured chair 12 is shown in FIGS. 5 and 6. A receiving structure 100 is affixed to the underside of base portion 40 and preferably to support bar 86 of internal frame 80 by any well known means, for example by bolts. Receiving structure 100 has two distinct channels for receiving a first center support bar 102 and a second center support bar 104 which support footrest assembly 20 and tray assembly 22, respectively. The use of center support bars allows improved viewing by a therapist of an occupant's pelvis and upper leg muscles and greater air circulation about base portion 40 in comparison with conventional tray and footrest support structures which typically rely on obstructing side structures to support a tray and/or footrest.

First center support bar 102 is removably secured within a first receiving channel in receiving structure 100 by selective engagement of spring biased peg 106 with peg receiving bores 108a, 108b, etc. located within one side of support bar 102. A similar arrangement is used to selectively secure second center support bar 104 in the second receiving channel in receiving structure 100, i.e., spring biased peg 110 selectively engages peg receiving bores 112a, 112b, 112c, etc. (see FIG. 6). As can be observed from FIGS. 5 and 6 the forward protrusion of central ridge 54 beyond front edge 56 of contoured chair 12 functions to partially protect an occupant from contacting first center support bar 102 and second center support bar 104 when they are secured to contoured chair 12.

Footrest assembly 20 will now be described with reference to the exploded view of FIG. 7. First center support bar 102 has a first arm 120 and a second arm 122 extending from first arm 120 at a fixed angle. First arm 120 includes the above discussed peg receiving bores 108a, 108b, 108c, 108d sized for selective engagement with spring biased peg 106. In addition, the end 121 of first arm 120 is preferrably beveled on that side having said peg receiving bores therein so that center support bar 102 may be easily inserted into receiving structure 100 with spring biased peg 106 automatically engaging that peg receiving bore 108d closest to the end of first arm 120.

As illustrated, a first cylindrical tube 124 slidably engages second arm 122. First cylindrical tube 124 is simply adjusted by first loosening threaded peg 126 and then retightening it after a desired adjustment along arm 122 has been made. Preferably a brake mechanism responsive to threaded peg 126 is employed which allows first cylindrical tube 124 to be infinitely adjusted within a range defined by the length of second arm 122. One disc brake mechanism which functions especially well for this purpose is illustrated in FIG. 8. This brake mechanism includes a bracket 128 which slidably envelops three sides of second arm 122, and a C-shaped bracket 130 adjustably connected to said enveloping bracket 128 and around the fourth side of second arm 122 such that when pressure is applied to C-shaped bracket 130 by appropriately turning threaded peg 126, C-shaped bracket 130 forces enveloping bracket 128 against second arm 122 to thereby maintain first cylinder 124 in a fixed position. It should be understood, however, that there are numerous other adjustable brake mechanisms which would adequately function in place of this braking mechanism without departing from the scope of the present invention.

In the preferred embodiment, footrest assembly 20 includes two independently movable, molded shoes 132a and 132b. Each shoe has partial side and back walls to assist in properly positioning an occupant's foot therein. The underside of each shoe 132a and 132b is appropriately molded so as to rotably engage first cylindrical tube 124. Shoes 132a and 132b are secured to first cylindrical tube 124 by screws 134a and 134b threaded through slots 135a and 135b, respectively, in first cylindrical tube 124. With such a design shoes 132a and 132b may be individually rotated about first cylindrical tube 124 by selectively loosening screws 134a and 134b and then by retightening said screws after a desired rotation has been made. It will be observed that by such rotation of footrests 132a and 132b about first cylindrical tube 124, a desired ankle dorsiflexion or plantiflexion of either one or both of an occupant's feet may be obtained. In addition, it should be observed that infinite adjustment of first cylindrical tube 124 along second arm 122 and selective adjustment of footrest assembly 20 relative to base portion 42 provide horizontal and vertical adjustments of footrests 132a and 132b relative to contoured chair 12. When an occupant is properly seated within contoured chair 12 such adjustments provide ready means for changing the occupant's hip flexion or hip extension.

As also shown in FIG. 7, a resilient bumper ball 136 is attached to the end of second arm 122 opposite from that end secured to first arm 120. Bumper ball 136 provides a surface for temporarily balancing seat support and restraint system 10 when it is being transported from one location to another. In addition, foot straps 137a and 137b are provided for securing an occupant's feet within shoes 132a and 132b, respectively. Foot straps 137a and 137b may be secured to shoes 132a and 132b in any well known manner. For example, loop-type and hook-type fabrics as discussed in connection with headrest 24 may be used.

An exploded view of tray assembly 22 is shown in FIG. 9. As noted in connection with FIG. 6, second center support bar 104 has a first end 140 which has peg receiving bores on one side for selective engagement with spring biased peg 110. Preferably, the edge 141 of first end 140 is beveled on that side having said peg receiving bores therein, similar to beveled end 121 in first arm 120 of first center support bar 102. A second end 142 of second center support bar 104 is secured to a second cylindrical tube or bar 144. Second center support bar 104 may be constructed of various shapes without departing from the scope of the present invention.

Tray 148 is rotably secured to second cylindrical tube 144 by brackets 146a and 146b which wrap about second cylindrical tube 144 and are affixed to the underside of tray 148. An extension arm 150 having a threaded bore 152 therein is secured at one end of second cylindrical tube 144 in a fixed position. A U-shaped bracket 154 having a U-shaped slot 155 therein is secured to the underside of tray 148 at a cooperative distance relative to extension arm 150. A threaded peg 156 is used to engage threaded bore 152 in extension arm 150 through U-shaped slot 155 such that when loosened, tray 148 may be adjustably rotated about second cylindrical tube 144 and when tightened tray 148 will remain at a fixed position relative to second cylindrical tube 144. As shown in FIG. 9, tray 148 preferably has a curbed edge 154 facing back portion 42 of contoured chair 12. When secured to contour chair 12 curved edge 154 of tray 148 may function to partially restrain an occupant's upper body should shoulder/trunk strap 28 not be in use.

It will be observed that selective engagement of spring biased peg 110 with peg receiving bores in first end 140 of second center support bar 104 provides a means for horizontally adjusting tray 148 relative to back portion 42. In addition, it should be observed that rotation of tray 148 about second cylindrical tube 144 allows the angle to be varied at which tray 148 is located relative to back portion 42. The horizontal and angle adjustments of tray 148 enable tray assembly 22 to be readily used by different occupants for various daily living activities.

Lastly, it should be noted that belt 18 may be used to position contoured chair 12 on conventional seating structure 14 in a plurality of positions (see FIG. 10). The underside 17 of contoured chair 12 where base portion 40 and back portion 42 meet is rounded to facilitate selective recline positioning of contoured chair 12 relative to conventional seating structure 14. Be being able to so selectively position contoured chair 12, the spacial location of an occupant within contoured chair 12 may be varied. Change in the spacial location of contoured chair 12 allows certain of the occupant's muscles to be selectively stressed or relaxed with therapeutic results.

It will be noted from the above that this invention fully meets the objectives set forth. A seat support and restraint system capable of properly aligning an occupant's muscles and skeletal frame through the integrated adjustment of parts is provided. Further, it will be noted that the disclosed seat support and restraint system is portable, capable of use in different environments, and adjustable to accommodate different occupants. Lastly, it will be observed that through the provision of proper body support and the alignment of muscles, the seat support and restraint system is capable of enhancing an occupant's performance of daily living skills.

Although one embodiment has been illustrated in the accompanying drawings and described in the foregoing description, it will be understood that the invention is not limited to the particular embodiment discussed but is capable of numerous rearrangements, modifications and substitutions without departing from the scope of the invention. Also, it should be emphasized that an individual of any age, such as an elderly patient, can benefit from use of the present invention. The following claims are intended to encompass all such modifications.

What is claimed is:

1. A seat support and restraint system capable of reducing neuromuscular dysfunction and skeletal deformation and facilitating therapy of a neurologically impaired occupant seated thereon, comprising:

a contoured chair having molded base and back portions, said base and back portions forming a continuous support surface;

said base portion having a first pair of side walls for laterally positioning an occupant's pelvis and maintaining an occupant's thighs in an adducted position, and having a seating surface including a rearward section and a forward section, said rearward section being recessed below said forward section for receiving an occupant's buttocks and being connected to said forward section by a continuous inclined ridge positioned and sized to engage an occupant's ischial tuberosities and thereby prevent forward pelvic movement, said forward section having a pair of troughs running forwardly from the rearward section and separated by a central ridge for supporting an occupant's thighs in an abducted position; and said back portion having a support surface including a lower section and an upper section, said lower section having a second pair of side walls having inwardly sloping surfaces for matable engagement with an occupant's trunk for orienting the occupant's trunk to midline, said upper section having a third pair of side walls continuous with and less protruding than said second pair of side walls, each side wall of said third pair terminating in an enlarged portion in opposed relation to the other side wall, said opposed enlarged portions defining a central cradle for receiving an occupant's neck and head, said upper section further having gradually inwardly sloping surfaces from said third pair of side walls for matable engagement with and slight inwardly curving of an occupant's shoulders, whereby said molded base and back portions of said contoured chair cooperate to firmly plant an occupant's pelvis and properly align the occupant's muscles and skeletal structure.

2. The seat support and restraint system of claim 1, wherein a first part of said lower back section adjacent said base portion is fixedly positioned with respect to said base portion and a second part of said lower back section adjacent said upper back section is adjustable along with said upper back section with respect to said base portion such that said back section is partially adjustable with respect to said base portion, while an occupant's pelvis remains in a fixed undisturbed position notwithstanding adjustment of said back portion relative to said base portion.

3. The seat support and restraint system of claim 2, wherein said angle of inclination is adjustable within a 30° range.

4. The seat support and restraint system of claim 1, further comprising an adjustable headrest removably secured to said back portion within said central cradle, said adjustable headrest having either a hook-type fabric or loop-type fabric secured to its backside and said central cradle having the other of said hook-type fabric or loop-type fabric secured to its support surface, said hook-type fabric and said loop-type fabric being capable of detachably fastening to each other.

5. The seat support and restraint system of claim 4, wherein said adjustable headrest has a U-shaped support face for matable engagement with an occupant's neck or head.

6. The seat support and restraint system of claim 1, further comprising means for securing said contoured chair to and upon a conventional chair.

7. The seat support and restraint system of claim 6, further comprising means for securing said contoured chair to and upon a vehicle's seating surface.

8. The seat support and restraint system of claim 1, further comprising:
an adjustable footrest assembly having separate foot receiving shoes infinitely adjustable in height within a predefined range such that once an occupant's pelvis is firmly planted, the height of said shoes can be adjusted to set the occupant's hip flexion; and
means for removably securing said adjustable footrest assembly to said base portion.

9. The seat support and restraint system of claim 8, wherein the spatial orientation of each of said footrest assembly receiving shoes is infinitely adjustable within a range defined by an occupant's normal range of ankle dorsiflexion and plantiflexion.

10. The seat support and restraint system of claim 1, further comprising:
an adjustable tray assembly; and
means for removably securing said adjustable tray assembly to said base portion.

11. The seat support and restraint system of claim 10, wherein said adjustable tray assembly comprises:
a tray;
a second cylindrical tube;
a second center support bar having a first end affixed to said second cylindrical tube and a second end capable of being secured to said base portion; and
means for rotably securing said tray to said second cylindrical tube such that the angle of said tray relative to said back portion may be varied.

12. The seat support and restraint system of claim 11, wherein said second end has a plurality of peg receiving bores on one side, and wherein said tray assembly securing means comprises a support bar receiving structure secured to said internal frame, said receiving structure having a second support bar receiving opening and a second spring loaded peg in engagable relation with said peg receiving bores in said second end such that said second center support bar may be secured within said second receiving opening in a plurality of positions.

13. The seat support and restraint system of claim 11, wherein said central ridge protrudes forwardly out from the forward section of said base portion to prevent an occupant's legs from contacting said second center support bar.

14. The seat support and restraint system of claim 1, further comprising:
an adjustable footrest assembly; and
means for removably securing said adjustable footrest assembly to said base portion.

15. The seat support and restraint system of claim 14, wherein said adjustable footrest assembly comprises:
a first cylindrical tube;
a footrest adjustably secured to said first cylindrical tube such that the positioning of said footrest may be varied about said tube;
a first center support bar having a first arm and a second arm depending therefrom at a fixed angle, said first arm capable of being secured to said base portion; and
means for adjustably securing said first cylindrical tube to said second arm such that the vertical position of said first cylindrical tube relative to said base portion may be varied.

16. The seat support and restraint system of claim 15, further comprising a molded bumper secured to the end of said second arm opposite from that end connected to said first arm, whereby the seat support and restraint system may be temporarily balanced on said molded bumper when said footrest assembly is secured to said contoured chair.

17. The seat support and restraint system of claim 15, wherein said central ridge protrudes forwardly out from the forward section of said base portion to prevent an occupant's legs from contacting said first center support bar.

18. The seat support and restraint system of claim 15, wherein said means for removably securing said footrest assembly to said base portion provides a plurality of securing positions such that the horizontal position of said first cylindrical tube relative to said base portion may be varied.

19. The seat support and restraint system of claim 18, wherein said first arm has a plurality of peg receiving bores on one side, and wherein said footrest assembly securing means comprises a support bar receiving structure secured to said internal frame, said receiving structure having a first support bar receiving opening and a first spring loaded peg in engagable relation with said peg receiving bores in said first arm such that said first center support bar may be secured within said first receiving opening in a plurality of positions.

20. The seat support and restraint system of calim 18, wherein said footrest comprises two distinct, molded shoes independently adjustable about said first cylindrical tube.

21. The seat support and restraint system of claim 20, further comprising foot straps for restraining an occupant's feet within said molded shoes.

22. The seat support and restraint system of claim 1, further comprising an L-shaped frame internal to said base and back portions of said contoured chair.

23. The seat support and restraint system of claim 22, wherein said base and back portions are molded of a resilient foam material.

24. The seat support and restraint system of claim 23, further comprising a flexible, seamless outer covering over said molded foam base and back portions.

25. The seat support and restraint system of claim 23, wherein said base and back portions are adjustable relative to each other.

26. The seat support and restraint system of claim 22, further comprising:
   a lap belt; and
   means for securing said lap belt to said contoured chair so that when in use said lap belt will be at approximately a 45° angle relative to said base portion, whereby said lap belt cooperates with said continuous inclined ridge to ensure that an occupant's pelvis remains fixed once properly positioned on said contoured chair.

27. The seat support and restraint system of claim 26, further comprising an adjustable shoulder/trunk belt assembly secured to said contoured chair for restraining an occupant's upper body.

28. The seat support and restraint system of claim 27, wherein said shoulder/trunk belt assembly rides within elongated slots at its upper end to automatically adjust for occupants of various height and weight within a predefined range.

29. The seat support and restraint system of claim 27, wherein said contoured chair has vertically extending slots in said back portion through which said adjustable shoulder/trunk belt assembly is secured to said back portion, and further comprising at least two loop belts, each loop belt being positioned within said contoured chair such as to encircle a portion of said internal frame and one of said vertically extending slots in said back portion, whereby said loop belts ensure securement of said adjustable shoulder/trunk belt assembly to the internal frame of said chair.

30. An adjustable seat support and restraint system capable of reducing neuromuscular dysfunction and skeletal deformation and facilitating therapy of a neurologically impaired occupant seated thereon, comprising:
   a contoured, portable chair having base and back portions molded of a resilent foam material, said base and back portions forming a substantially continuous support surface capable of firmly planting an occupant's pelvis;
   a frame internal to said base and back portions, said frame having a top portion and a L-shaped bottom portion, said top portion being pivotally adjustable relative to said bottom portion; and
   a footrest assembly adjustably secured to said base portion of said contoured chair, whereby said contoured chair and said internal frame and footrest assembly adjustments cooperate to allow an occupant's muscles and skeletal structure to be properly aligned while restraining an occupant's pelvis in a fixed position.

31. The adjustable seat support and restraint system of claim 30, wherein the top portion of said internal frame is adjustable within a 30° range relative to the bottom portion of said frame.

32. The adjustable seat support and restraint system of claim 30, further comprising an adjustable headrest removably secured to said chair back portion and having a U-shaped support face for matable engagement with an occupant's head or neck, said headrest also having a hook-type fabric secured to its back side and said back portion having a loop-type fabric secured to its support surface, said loop-type fabric and said hook-type fabric being capable of detachably fastening to each other.

33. The adjustable seat support and restraint system of claim 30, wherein said adjustable footrest assembly comprises:
   a first cylindrical tube;
   two distinct, molded shoes secured to said first cylindrical tube, said footrests being independently adjustable about said first cylindrical tube;
   a first center support bar having a first arm and a second arm depending therefrom at a fixed angle, said first arm being secured to said base portion; and
   means for adjustably securing said first cylindrical tube to said second arm such that the vertical position of said first cylindrical tube relative to said base portion may be varied.

34. The adjustable seat support and restraint system of claim 33, wherein said first arm may be selectively secured to said base portion in a plurality of positions such that the horizontal position of said first cylindrical tube relative to said base portion may be varied.

35. The adjustable seat support and restraint system of claim 30, further comprising an adjustable tray assembly secured to said base portion of said contoured chair.

36. The seat support and restraint system of claim 35 wherein said tray assembly comprises:
   a tray;
   a second cylindrical tube; -
   a second center support bar having a first end affixed to said second cylindrical tube and a second end secured to said base portion; and
   means for rotably securing said tray to said second cylindrical tube such that the angle of said tray relative to said back portion may be varied.

37. The adjustable seat support and restraint system of claim 30 further comprising:
   an adjustable lap belt for restraining an occupant's pelvis in a fixed position; and
   an adjustable shoulder/trunk belt assembly for restraining an occupant's upper body.

38. The adjustable seat support and restraint system of claim 37, wherein said contoured, portable chair has vertically extending slots in said back portion through which said adjustable shoulder/trunk belt assembly is secured to said back portion, and further comprising at least two loop belts, each loop belt being positioned within said contoured, portable chair such as to encircle a portion of said internal frame and one of said vertically extending slots in said back portion, whereby said loop belts ensure securement of said adjustable shoulder/trunk belt assembly to the internal frame of said contoured, portable chair.

39. The adjustable seat support and restraint system of claim 37, further comprising:
   means for securing said contoured, portable chair to and upon a conventional chair; and
   means for securing said contoured, portable chair to and upon a vehicle's seating surface.

40. An adjustable seat support and restraint system capable of reducing neuromuscular dysfunction and skeletal deformation and facilitating therapy of a neurologically impaired occupant seated thereon comprising:
   a contoured chair having molded base and back portions, said base and back portions forming a substantially continuous support surface;
   said base portion having a first pair of side walls for laterally positioning an occupant's pelvis and maintaining an occupant's thighs in an abducted position, and having a seating surface including a rearward section and a forward section, said rearward section being recessed below said forward section for receiving an occupant's buttocks and connected to said forward section by a continuous inclined ridge positioned and sized to engage an occupant's ischial tuberosities and thereby prevent forward pelvic movement, said forward section having a pair of troughs running forwardly from the rearward section and separated by a central ridge for supporting an occupant's thighs in abducted position;
   said back portion having a support surface including a lower section and an upper section, said lower section having a second pair of said walls having inwardly sloping surfaces for matable engagement with an occupant's trunk for orienting the occupant's trunk to midline, said upper section having a third pair of side walls continuous with and less protruding than said second pair of side walls, each side wall of said third pair terminating an enlarged portion in opposed relation to the other side wall, said opposed enlarged portions defining a central cradle for receiving an occupant's neck and head, said upper section further having gradually inwardly sloping surfaces from said third pair of side walls for matable engagement with and slight inwardly curving of an occupant's shoulders;
   a frame internal to said base and back portions, said frame having a top portion and an L-shaped bottom portion, said top portion being pivotally adjustable relative to said bottom portion; and
   a removable, adjustable footrest assembly secured to said base portion of said contoured chair, whereby said contoured chair and said internal frame and footrest assembly adjustments cooperate to firmly plant an occupant's pelvis and properly align the occupant's muscles and skeletal structure.

* * * * *

UNITED STATES PATENT AND TRADEMARK OFFICE
CERTIFICATE OF CORRECTION

PATENT NO. : 4,750,478

DATED : June 14, 1988

INVENTOR(S) : Timothy J. Bergeron

It is certified that error appears in the above-identified patent and that said Letters Patent is hereby corrected as shown below:

In claim 20, line 1, "calim" should be --claim--.

In claim 40, line 19, "abducted" should be --adducted--.

In column 16, line 5, "said" should be --side--.

Signed and Sealed this

Third Day of January, 1989

Attest:

DONALD J. QUIGG

Attesting Officer

Commissioner of Patents and Trademarks